United States Patent
Wolters et al.

(10) Patent No.: US 9,649,198 B2
(45) Date of Patent: May 16, 2017

(54) SPINAL INTERBODY IMPLANT WITH BONE SCREW RETENTION

(71) Applicant: Life Spine, Inc., Huntley, IL (US)

(72) Inventors: Madeline C. Wolters, Carol Stream, IL (US); James A. Rinner, Franksville, WI (US); Michael S. Butler, St. Charles, IL (US); Seetal K. Erramilli, Naperville, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 14/686,138

(22) Filed: Apr. 14, 2015

(65) Prior Publication Data
US 2015/0216674 A1   Aug. 6, 2015

Related U.S. Application Data

(63) Continuation of application No. 13/459,137, filed on Apr. 28, 2012, now Pat. No. 9,017,412.
(Continued)

(51) Int. Cl.
*A61F 2/44* (2006.01)
*A61F 2/30* (2006.01)

(52) U.S. Cl.
CPC ............ *A61F 2/4455* (2013.01); *A61F 2/442* (2013.01); *A61F 2/447* (2013.01); *A61F 2/30771* (2013.01);
(Continued)

(58) Field of Classification Search
CPC ...... A61F 2/442; A61F 2/4455; A61F 2/4465; A61F 2/447; A61F 2002/4475;
(Continued)

(56) References Cited

U.S. PATENT DOCUMENTS 2,383,141 A   8/1945   Maage, Jr.
2,401,856 A   6/1946   Brock
(Continued)

FOREIGN PATENT DOCUMENTS

CH          674927 A5     8/1990
DE       29 33 141 A1     4/1980
(Continued)

OTHER PUBLICATIONS

International Search Report for International Application No. PCT/US04/43172, dated Nov. 1, 2005, 4 pages.

*Primary Examiner* — Lynnsy Summitt
(74) *Attorney, Agent, or Firm* — Foley & Lardner LLP

(57) ABSTRACT

A spinal interbody implant has a bone screw retention mechanism that prohibits bone screws from backing out after the bone screws are installed. A bone screw retention plate is received in a plate retention area of the implant to provide a barrier that keeps the installed bone screws from backing out of their bone screw pocket. The bone screw retention mechanism consists of a retention plate and a configured plate retention area in a face of the implant body. Retention plate fasteners may be used to retain the configured plate. In one form, the bone screw retention mechanism consists of a retention plate, a configured plate retention area in a face of the implant body, and a retention plate bolt. In another form, the bone screw retention mechanism consists of a retention plate, a configured plate retention area in a face of the implant body, and a retention plate bolt.

17 Claims, 11 Drawing Sheets

Related U.S. Application Data

(60) Provisional application No. 61/480,474, filed on Apr. 29, 2011, provisional application No. 61/600,258, filed on Feb. 17, 2012.

(52) U.S. Cl.
CPC ........... *A61F 2002/3008* (2013.01); *A61F 2002/30135* (2013.01); *A61F 2002/30182* (2013.01); *A61F 2002/30187* (2013.01); *A61F 2002/30365* (2013.01); *A61F 2002/30439* (2013.01); *A61F 2002/30481* (2013.01); *A61F 2002/30482* (2013.01); *A61F 2002/30492* (2013.01); *A61F 2002/30517* (2013.01); *A61F 2002/30616* (2013.01); *A61F 2002/30617* (2013.01); *A61F 2002/30787* (2013.01); *A61F 2002/30807* (2013.01); *A61F 2002/30904* (2013.01); *A61F 2002/4475* (2013.01); *A61F 2220/0016* (2013.01); *A61F 2310/00017* (2013.01); *A61F 2310/00023* (2013.01)

(58) Field of Classification Search
CPC .. A61F 2002/30794; A61F 2002/30517; A61F 2002/30492
See application file for complete search history.

(56) References Cited

U.S. PATENT DOCUMENTS

| | | | |
|---|---|---|---|
| 3,741,205 A | 6/1973 | Markolf et al. | |
| 4,298,993 A | 11/1981 | Kovaleva et al. | |
| 4,388,921 A | 6/1983 | Sutter et al. | |
| 4,794,918 A | 1/1989 | Wolter | |
| 4,808,185 A | 2/1989 | Penenberg et al. | |
| 4,904,261 A | 2/1990 | Dove et al. | |
| D313,471 S | 1/1991 | Bremer et al. | |
| 5,197,839 A | 3/1993 | Willey et al. | |
| 5,364,399 A | 11/1994 | Lowery et al. | |
| 5,514,180 A | 5/1996 | Heggeness et al. | |
| 5,534,027 A | 7/1996 | Hodorek | |
| 5,888,223 A | 3/1999 | Bray, Jr. | |
| 5,951,558 A | 9/1999 | Fiz | |
| 6,099,531 A | 8/2000 | Bonutti | |
| 6,139,550 A | 10/2000 | Michelson | |
| 6,152,927 A | 11/2000 | Farris et al. | |
| 6,193,721 B1 | 2/2001 | Michelson | |
| 6,224,602 B1 | 5/2001 | Hayes | |
| 6,228,085 B1 | 5/2001 | Theken et al. | |
| 6,235,034 B1 | 5/2001 | Bray | |
| 6,258,089 B1 | 7/2001 | Campbell et al. | |
| 6,273,889 B1 | 8/2001 | Richelsoph | |
| 6,306,136 B1 | 10/2001 | Baccelli | |
| 6,364,881 B1 | 4/2002 | Apgar et al. | |
| 6,398,783 B1 | 6/2002 | Michelson | |
| 6,402,756 B1 | 6/2002 | Ralph et al. | |
| 6,413,259 B1 | 7/2002 | Lyons et al. | |
| 6,423,063 B1 | 7/2002 | Bonutti | |
| 6,428,542 B1 | 8/2002 | Michelson | |
| 6,432,106 B1 | 8/2002 | Fraser | |
| 6,447,544 B1 | 9/2002 | Michelson | |
| 6,454,769 B2 | 9/2002 | Wagner et al. | |
| 6,503,250 B2 | 1/2003 | Paul | |
| 6,533,786 B1 | 3/2003 | Needham et al. | |
| 6,599,290 B2 | 7/2003 | Bailey et al. | |
| 6,602,257 B1 | 8/2003 | Thramann | |
| 6,620,163 B1 | 9/2003 | Michelson | |
| 6,629,998 B1 | 10/2003 | Lin | |
| 6,669,700 B1 | 12/2003 | Farris et al. | |
| 6,695,846 B2 | 2/2004 | Richelsoph et al. | |
| 6,730,127 B2 | 5/2004 | Michelson | |
| D510,260 S | 10/2005 | Jennings et al. | |
| 6,974,460 B2 | 12/2005 | Carbone et al. | |
| 7,001,385 B2 | 2/2006 | Bonutti | |
| 7,232,463 B2 | 6/2007 | Falahee | |
| 7,780,670 B2 | 8/2010 | Bonutti | |
| D625,977 S | 10/2010 | Watson et al. | |
| 7,862,614 B2 | 1/2011 | Keller et al. | |
| 7,862,616 B2* | 1/2011 | Lechmann | A61B 17/86 623/17.11 |
| 7,892,261 B2 | 2/2011 | Bonutti | |
| 7,972,363 B2 | 7/2011 | Moskowitz et al. | |
| 8,137,405 B2 | 3/2012 | Kostuik et al. | |
| D658,046 S | 4/2012 | Austin, III | |
| 8,182,539 B2 | 5/2012 | Tyber et al. | |
| 8,419,778 B2* | 4/2013 | Barry | A61B 17/8605 606/267 |
| 8,419,797 B2* | 4/2013 | Biedermann | A61B 17/8047 606/289 |
| 8,603,145 B2* | 12/2013 | Forton | A61B 17/7035 606/251 |
| D706,127 S | 6/2014 | Hohmann, Jr. | |
| 8,784,498 B2 | 7/2014 | Scheland | |
| 8,882,813 B2* | 11/2014 | Jones | A61B 17/7059 606/289 |
| 8,956,417 B2 | 2/2015 | Bonutti | |
| 9,017,412 B2 | 4/2015 | Wolters et al. | |
| 9,044,341 B2 | 6/2015 | Bonutti | |
| 9,364,342 B2* | 6/2016 | Walkenhorst | A61F 2/4465 |
| 2001/0041894 A1 | 11/2001 | Campbell et al. | |
| 2002/0045896 A1 | 4/2002 | Michelson | |
| 2002/0045899 A1 | 4/2002 | Errico et al. | |
| 2002/0111630 A1 | 8/2002 | Ralph et al. | |
| 2002/0120273 A1 | 8/2002 | Needham et al. | |
| 2002/0128655 A1 | 9/2002 | Michelson | |
| 2002/0143336 A1 | 10/2002 | Hearn | |
| 2002/0147450 A1 | 10/2002 | LeHuec et al. | |
| 2002/0151899 A1 | 10/2002 | Bailey et al. | |
| 2002/0183754 A1 | 12/2002 | Michelson | |
| 2002/0183755 A1 | 12/2002 | Michelson | |
| 2002/0183756 A1 | 12/2002 | Michelson | |
| 2002/0183757 A1 | 12/2002 | Michelson | |
| 2002/0188296 A1 | 12/2002 | Michelson | |
| 2003/0023242 A1 | 1/2003 | Harrington, Jr. | |
| 2003/0040749 A1 | 2/2003 | Grabowski et al. | |
| 2003/0060828 A1 | 3/2003 | Michelson | |
| 2003/0083658 A1 | 5/2003 | Hawkes et al. | |
| 2003/0105462 A1 | 6/2003 | Haider | |
| 2003/0105526 A1 | 6/2003 | Bryant et al. | |
| 2004/0034356 A1 | 2/2004 | LeHuec et al. | |
| 2004/0068319 A1 | 4/2004 | Cordaro | |
| 2004/0087951 A1 | 5/2004 | Khalili | |
| 2004/0102773 A1 | 5/2004 | Morrison et al. | |
| 2004/0122426 A1 | 6/2004 | Michelson | |
| 2004/0127896 A1 | 7/2004 | Lombardo et al. | |
| 2004/0127897 A1 | 7/2004 | Freid et al. | |
| 2004/0127899 A1 | 7/2004 | Konieczynski et al. | |
| 2004/0181226 A1 | 9/2004 | Michelson | |
| 2004/0181229 A1 | 9/2004 | Michelson | |
| 2004/0186476 A1 | 9/2004 | Michelson | |
| 2004/0204712 A1 | 10/2004 | Kolb et al. | |
| 2004/0220571 A1 | 11/2004 | Assaker et al. | |
| 2004/0220572 A1 | 11/2004 | Michelson | |
| 2004/0236335 A1 | 11/2004 | Michelson | |
| 2005/0027297 A1 | 2/2005 | Michelson | |
| 2005/0027298 A1 | 2/2005 | Michelson | |
| 2005/0033298 A1 | 2/2005 | Hawkes et al. | |
| 2005/0043732 A1 | 2/2005 | Dalton | |
| 2005/0059971 A1 | 3/2005 | Michelson | |
| 2005/0075633 A1 | 4/2005 | Ross | |
| 2006/0162506 A1 | 7/2006 | Kirchgaessler | |
| 2006/0206208 A1* | 9/2006 | Michelson | A61B 17/7059 623/17.11 |
| 2008/0149569 A1 | 6/2008 | Rai et al. | |
| 2008/0249569 A1 | 10/2008 | Waugh et al. | |
| 2009/0088808 A1* | 4/2009 | Lindemann | A61B 17/7059 606/286 |
| 2009/0105830 A1 | 4/2009 | Jones et al. | |
| 2009/0287249 A1* | 11/2009 | Reynolds | A61B 17/7059 606/246 |
| 2010/0106249 A1* | 4/2010 | Tyber | A61F 2/447 623/17.11 |

(56) References Cited

U.S. PATENT DOCUMENTS

| | | | |
|---|---|---|---|
| 2010/0145459 A1* | 6/2010 | McDonough | A61B 17/8033 623/17.16 |
| 2010/0145460 A1* | 6/2010 | McDonough | A61B 17/8033 623/17.16 |
| 2010/0152785 A1* | 6/2010 | Forton | A61B 17/8605 606/301 |
| 2010/0249935 A1* | 9/2010 | Slivka | A61F 2/4611 623/17.16 |
| 2010/0312345 A1* | 12/2010 | Duffield | A61F 2/447 623/17.16 |
| 2011/0009966 A1* | 1/2011 | Michelson | A61F 2/4455 623/17.11 |
| 2011/0166658 A1* | 7/2011 | Garber | A61F 2/4465 623/17.16 |
| 2011/0178559 A1* | 7/2011 | Barry | A61B 17/7038 606/302 |
| 2011/0230969 A1 | 9/2011 | Biedermann et al. | |
| 2012/0065734 A1* | 3/2012 | Barrett | A61F 2/4455 623/17.16 |
| 2012/0126532 A1 | 5/2012 | Herndon | |
| 2012/0203348 A1* | 8/2012 | Michelson | A61B 17/7059 623/17.16 |
| 2012/0215318 A1* | 8/2012 | Michelson | A61F 2/4611 623/17.16 |
| 2012/0232599 A1* | 9/2012 | Schoenly | A61B 17/8635 606/315 |
| 2012/0265301 A1 | 10/2012 | Demers et al. | |
| 2013/0218279 A1* | 8/2013 | Michelson | A61B 17/7059 623/17.16 |
| 2013/0245688 A1* | 9/2013 | Biedermann | A61B 17/8047 606/246 |
| 2013/0268008 A1* | 10/2013 | McDonough | A61B 17/8033 606/279 |
| 2014/0142705 A1* | 5/2014 | Duffield | A61F 2/447 623/17.16 |
| 2014/0163684 A1* | 6/2014 | Donner | A61B 17/70 623/17.16 |
| 2015/0025637 A1* | 1/2015 | Moskowitz | A61B 17/0642 623/17.16 |
| 2015/0032115 A1* | 1/2015 | Laposta | A61B 17/8894 606/99 |
| 2015/0164564 A1 | 6/2015 | Reiley | |
| 2015/0216675 A1* | 8/2015 | McDonough | A61B 17/8033 623/17.16 |
| 2015/0238317 A1 | 8/2015 | Bonutti | |
| 2015/0305883 A1* | 10/2015 | Garber | A61F 2/4465 623/17.16 |

FOREIGN PATENT DOCUMENTS

| | | |
|---|---|---|
| EP | 0 179 695 A1 | 4/1986 |
| EP | 0 313 762 A1 | 5/1989 |
| FR | 2651996 A3 | 3/1991 |
| WO | WO-91/03994 A1 | 4/1991 |
| WO | WO-95/30389 A1 | 11/1995 |
| WO | WO-96/03096 A1 | 2/1996 |
| WO | WO-96/23457 A1 | 8/1996 |

* cited by examiner

SPINAL INTERBODY IMPLANT WITH BONE SCREW RETENTION

CROSS-REFERENCE TO RELATED PATENT APPLICATIONS

This application is a continuation of application Ser. No. 13/459,137, filed Apr. 28, 2012, which claims the benefit of Provisional Application No. 61/480,474, filed Apr. 29, 2011 and Provisional Application No. 61/600,258, filed Feb. 17, 2012, all of which are incorporated herein by reference in their entirety.

BACKGROUND

The present invention relates to spinal implants for implantation between a pair of adjacent vertebrae in order to provide support to the vertebrae and/or promote bone fusion between the vertebrae.

Because of disease, injury or deformity the disc that is between adjacent vertebrae of the human spine may become damaged. Additionally, the disc may simply deteriorate due to age or congenital defect. In these and in other circumstances, one or more vertebrae may become compressed or otherwise damaged. Moreover, the vertebrae can become too closely spaced which causes an undesired abnormal curvature of the spine. Such conditions may also cause a nerve to be pinched, creating pain, numbness and/or other symptoms. In these situations it is then necessary to provide support and/or alignment to and between adjacent vertebrae of the patient's spine. This is generally accomplished through spinal surgery.

With spinal surgery, one or more spinal implants, spacers, intervertebral devices or interbody devices (collectively, interbody devices) are placed between adjacent vertebrae once the disc has been removed. This provides proper spacing of the vertebrae. The interbody device may also promote fusion between the adjacent vertebrae.

Once the interbody device has been implanted into the intervertebral space, it is important that the interbody device remain in its implanted position. This is accomplished by using bone screws that extend through the interbody device and into the vertebral bone. Typically, one or more bone screws extend through the interbody device and into vertebral bone of an upper, adjacent vertebra and a lower, adjacent vertebra. Because the bone screws are oriented in a particular manner in order to fix the interbody device relative to and between the adjacent vertebrae, it is vital that the bone screws do not back out while implanted.

Accordingly, there exists a need for an interbody device that remains in place once implanted and provides stabilization and torsional resistance in order to promote vertebral fusion. Moreover, there exists a need for an interbody device that retains its bone screws once installed.

SUMMARY

The present invention is a spinal interbody implant having a bone screw retention mechanism that prohibits bone screws from reversing (backing out) after the bone screws are installed.

The bone screw retention mechanism includes a bone screw retention plate that is received in a plate retention area of the spinal interbody implant to provide a barrier for keeping the installed bone screws from backing out of their respective bone screw pockets of the spinal interbody implant.

In one form, the bone screw retention mechanism consists of a retention plate and a configured plate retention area in a face of the implant body, while in another form the bone screw retention mechanism consists of a retention plate, retention plate fasteners and a configured plate retention area in the face of the implant body.

The bone screw retention plate may be formed as a flexible plate with a predetermined curvature that snaps into the corresponding configured plate retention area in the front face of the implant body. The bone screw retention plate may alternately be formed as a rigid plate having a predetermined shape that fits into the corresponding configured plate retention area in the front face of the implant body. In this form, the retention plate fasteners are used to releasably secure the rigid plate into the configured plate retention area of the implant body.

The configured plate retention area is formed by undercuts machined into the front face of the spinal interbody implant. The configured plate retention area additionally includes an undercut in each lateral side of the configured plate retention area in the implant body face when the flexible retention plate is used in order to accept and retain the ends of the flexible retention plate in the configured plate retention area. Alternately, the configured plate retention area additionally includes two undercuts within the configured plate retention area in the implant body face when the rigid retention plate is used in order to accept the retention plate fasteners.

The retention plate fasteners are fashioned as cams that are rotatably carried by the retention plate. Each cam has a nub that helps to maintain its rotational position relative to the retention plate. Particularly, the cam is rotatable such that its nub is positionable in one of two indents that are located 90° to one another about cam bores located in cam bosses of the retention plate. The nub of a cam thus rests in one of the two indents where one indent provides an unlocked position and the other indent provides a locked position. When the cam is rotated the nub applies pressure to the lock plate wall causing it to deflect. Turned into the locked position the nub rests in the "lock" indent while a nose of the retention plate fastener is engaged in the undercuts of the plate retention area. Turned into the unlocked position the nub rests in the "unlock" indent while the nose of the retention plate fastener is disengaged from the undercuts of the plate retention area.

Each retention plate fastener has a configured bore that allows the introduction of a configured driver tool for rotating the retention plate fastener between the unlocked and locked positions. Indicia on both the retention plate and the retention plate fasteners provide a visual indicator of the unlocked and locked states/positions of the retention plate fasteners and thus the retention plate. The indicia may also or alternately have a portion that shows the direction of rotation of the retention plate fastener that will effect locking (vice versa or both).

In another form, the bone screw retention mechanism consists of a retention plate, a configured plate retention area in a face of the implant body, and a retention plate bolt.

The bone screw retention plate is formed as a generally planar, rigid plate that fits into the corresponding configured plate retention area in the front face of the implant body. The bone screw retention plate may alternately be formed as a planar semi-rigid plate having a predetermined shape that fits into the corresponding configured plate retention area in the front face of the implant body. In both cases, the plate has a hub with a first arm extending from one side of the hub, and a second arm extending from another side of the hub, generally opposite the first arm. A bore in the hub allows receipt of the plate fastener for attaching the plate to the implant body. When implanted, the first and second arms extend over respective bone screw bores and bone screws in the bores.

The plate retention area is formed by slots in the front face of the implant body. The plate retention area additionally includes an internally threaded bore that receives the plate fastener. When installed, the bone screw retention mechanism is generally flush with the implant body.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

Figure 1:
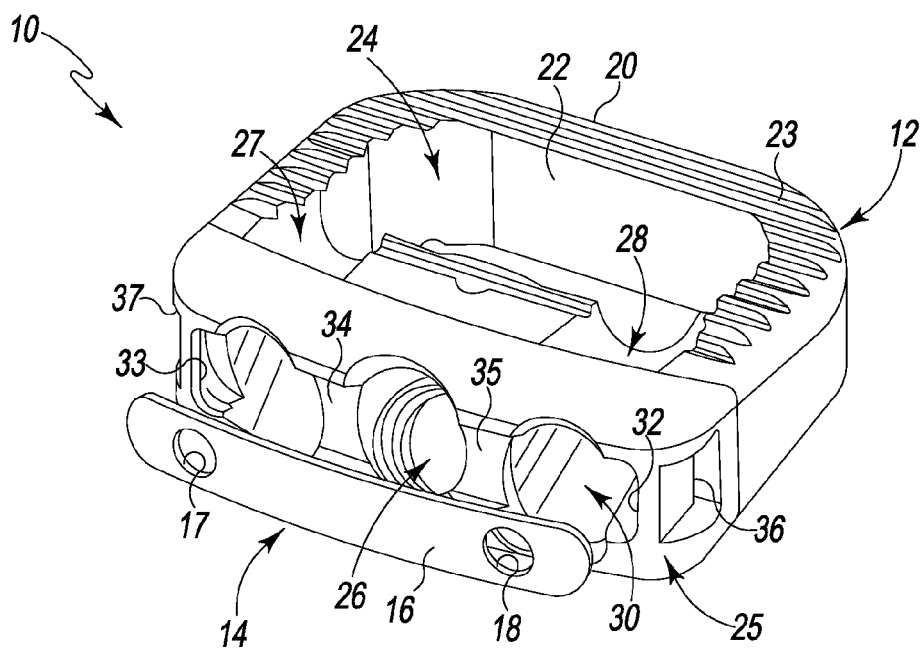
FIG. 1 is an isometric view of a spinal interbody implant having an embodiment of a bone screw retention mechanism with a bone screw retention plate thereof depicted in an uninstalled position.
Figure 2:
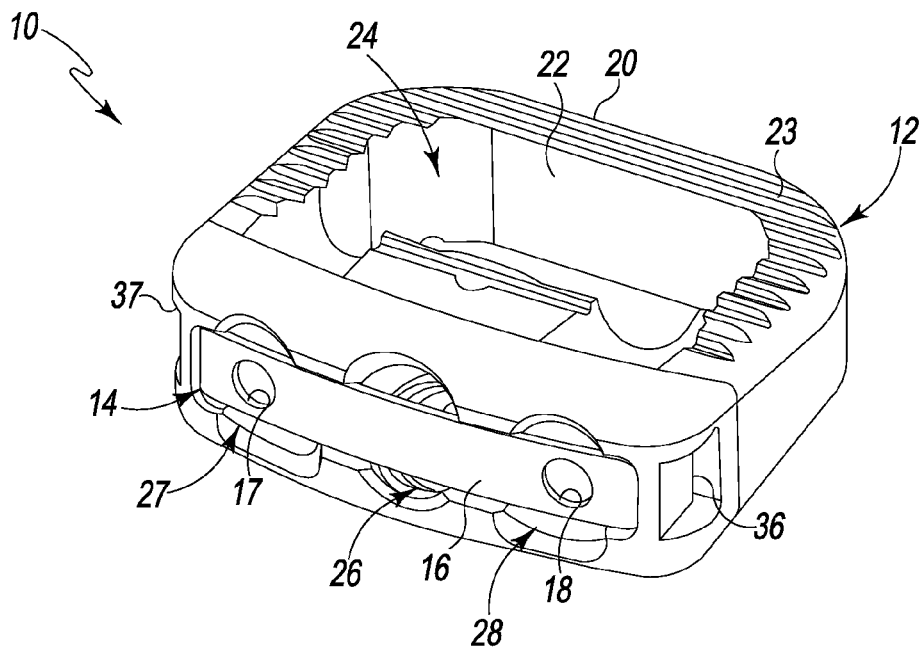
FIG. 2 is the isometric view of the spinal interbody implant of FIG. 1 with the bone screw retention plate in an installed position.

A detailed description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Referring to the Figures and in particular to FIGS. 1-5, there is depicted an exemplary spinal interbody implant, generally designated 10, that incorporates a bone screw retention mechanism fashioned in accordance with the present principles. The spinal interbody implant 10 comprises an implant 12 and a bone screw retention mechanism defined by a bone screw retention plate 14 and a configured retention plate reception area 30 formed in a posterior face 25 of the implant 12.

The implant 12 is defined a body 20 that is fabricated from a bio-compatible material such as stainless steel, titanium, a titanium alloy, composite, polymer or the like. The implant body 20 is sized to be received between adjacent vertebrae but to not extend beyond the periphery of the vertebra. As such, the implant body 20 may be fabricated in various sizes to accommodate various sizes of vertebrae.

The implant body 20 has an essentially D-shaped wall 22 with a serrated upper surface 23 and a like serrated lower surface (not seen in the figures). The D-shaped wall 22 defines an essentially D-shaped void 24 within its interior. The implant body 20 has several bone screw pockets or bores 26, 27, 28 each of one which is configured to receive a bone screw (not shown) therein. Particularly, the implant body 20 has a middle bone screw pocket or bore 26 that extends from the posterior face 25 and angles downwardly (in the inferior direction when implanted) into the void 24, a first lateral bone screw pocket or bore 27 that extends from the posterior face 25 and angles upwardly (in the superior direction when implanted) into the void 24, and a second lateral bone screw pocket or bore 28 that extends from the posterior face and angles upwardly (in the superior direction when implanted) into the void 24. The bone screw pockets 26, 27, 28 allow the shank of a bone screw to extend through and out of the respective bore but not allow the heads thereof to ingress into the void 24. It should be appreciated that the nomenclature first and second is arbitrary.

The implant body 20 further includes a first configured notch 36 formed in a first front lateral corner thereof and a second configured notch 37 formed in a second front lateral corner thereof. Again, it should be appreciated that the nomenclature first and second is arbitrary. The first and second configured notches 36, 37 are situated on and shaped so as to allow the implant body 20 to be implanted between adjacent vertebrae (not shown) via an implant tool (not shown).

As best seen in FIG. 1, the retention plate 14 is defined by a generally elongated oval body 16 having a thickness that allows the retention plate 14 to be flexible but resilient. The retention plate 14 is fabricated from a bio-compatible material such as stainless steel, titanium, a titanium alloy, composite, polymer or the like in a manner that allows such flexibility/resiliency. The body 16 includes a first bore 17 which, when the retention plate 14 is installed in the retention area 30 (see FIG. 2), allows access to the first lateral bone screw pocket 27 and thus the head of the bone screw (not shown) that is held therein. The body 16 also includes a second bore 18 which, when the retention plate 14 is installed in the retention area 30 (see FIG. 2), allows access to the second lateral bone screw pocket 28 and thus the head of the bone screw (not shown) that is held therein. As described more fully below, the retention plate 14 is flex fit into the retention area 30 such that the rounded ends of the body 16 extend and fit into configured undercuts 32, 33 in the front face 25.

Figure 3:
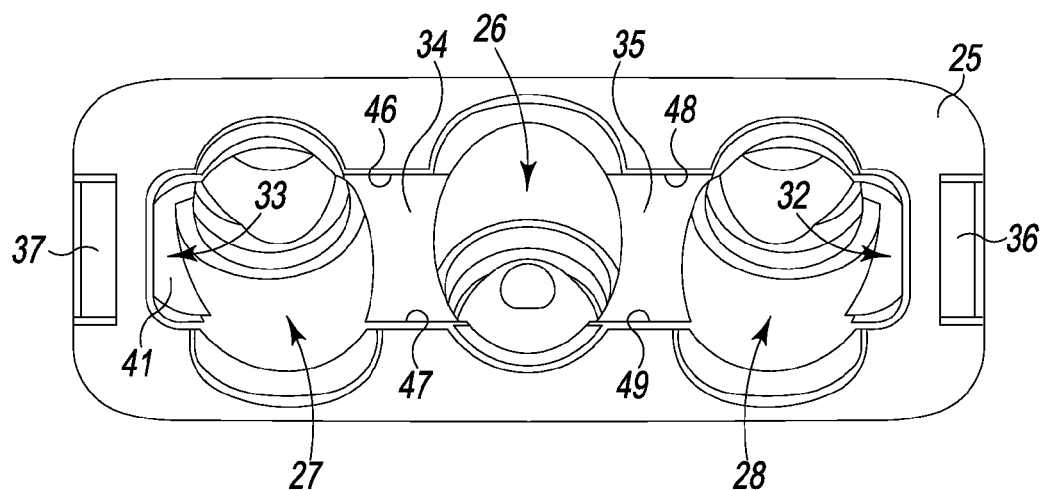
FIG. 3 is a front plan view of the spinal interbody implant of FIG. 1 with the bone screw retention plate removed.
Figure 4:
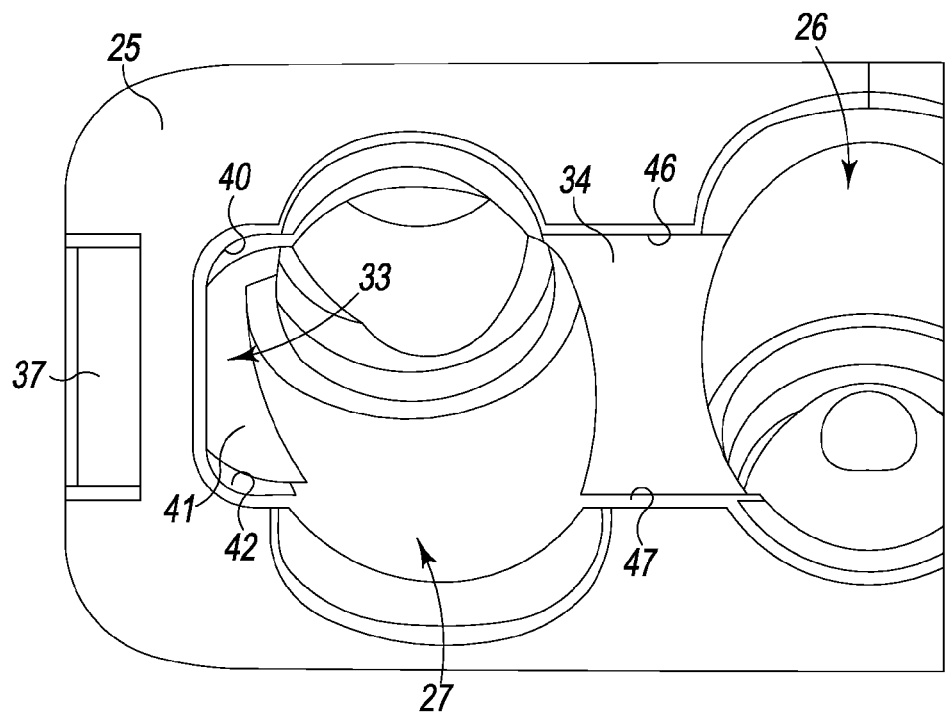
FIG. 4 is an enlarged partial front plan view of the spinal interbody implant of FIG. 3.
Figure 5:
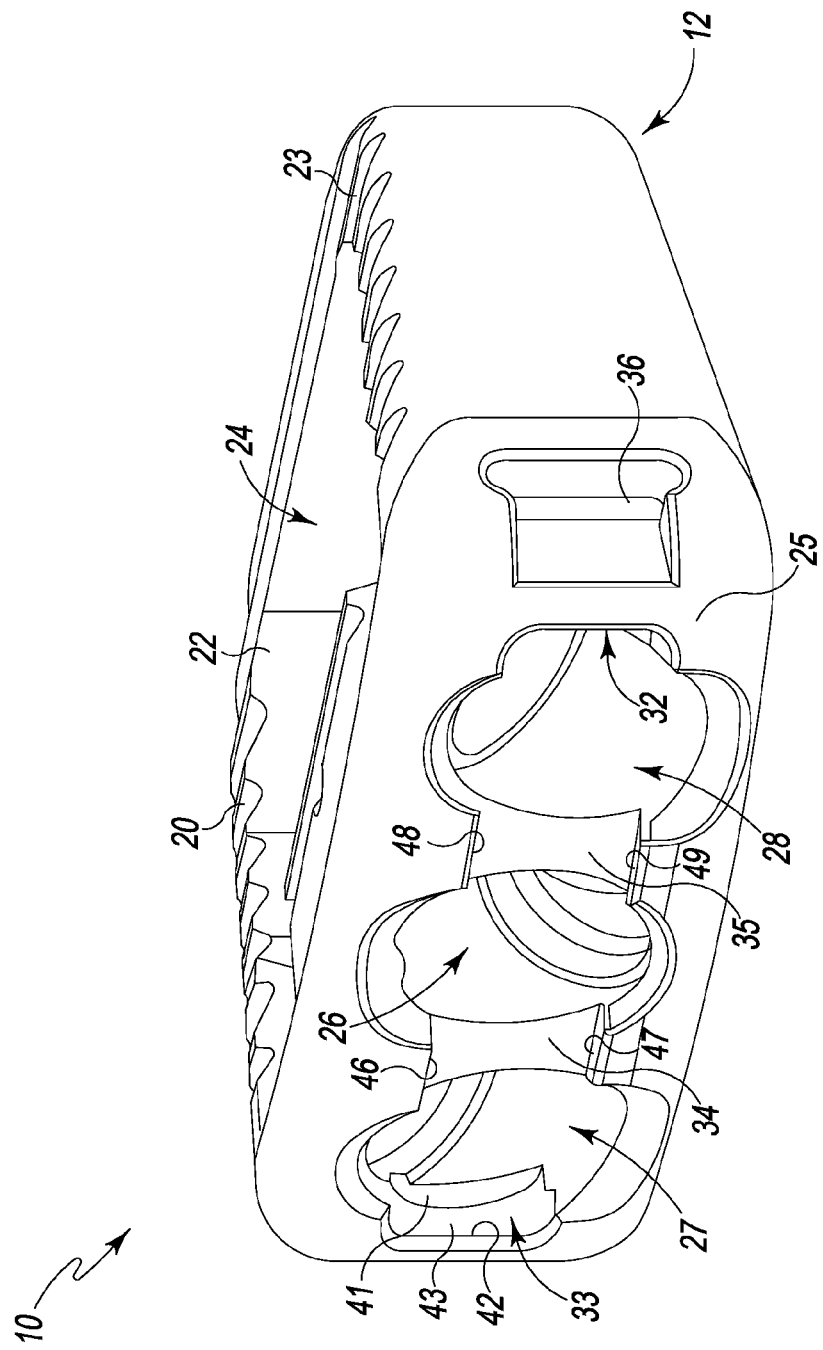
FIG. 5 is an enlarged isometric view of the present spinal interbody implant with the bone screw retention plate removed.

As indicated above, the retention area 30 of the implant body 20 is configured to receive the retention plate 14 particularly after bone screws (not shown) have secured the implant body 20 to the adjacent upper and lower vertebrae (not shown). With particular reference to FIGS. 3-5, the retention area 30 is defined in the front face 25 of the implant body 20. The front face 25 has a slight curvature which is likewise provided by the retention area 30. The retention area 30 consists of a first undercut area 32 in a first lateral side of the front face 25, a second undercut area 33 in a second lateral side of the front face 25, a first intermediate channel 35 defined between upper and lower ledges 48, 49, and a second intermediate channel 34 defined between upper and lower ledges 46, 47. Again, the nomenclature first and second is arbitrary. The retention plate 14 thus has a height that is received in the first and second intermediate channels 35, 34 between the respective ledges 48, 49 and 46, 47.

The first undercut area 32 and the second undercut area 33 have the same features. Therefore, it should be appreciated that the present discussion of the second undercut area 33 applies to the first undercut area 32. The second undercut area 33 has a flat 41 having the same curvature as the front face 25 and an end wall 43 that is curved in the same manner as the end of the retention plate 14. A front overhang 42 extends laterally so as to capture/retain the end of the retention plate 14. Once the implant body 20 has been implanted and secured with bone screws, the retention plate 14 is flexed and situated into the retention area 30. Release of the flexed retention plate 14 causes the ends thereof to be captured in the respective undercut area. The back side/surface of the retention plate 14 is adjacent to and/or abuts at least a portion of the heads of the installed bone screws such that back out of an installed bone screw is not possible. The retention plate 14 thus provides a barrier against the backing out of the installed bone screws.

Referring now to FIGS. 6-11 of the Figures, there is depicted another exemplary spinal interbody implant, generally designated 110, that incorporates a bone screw retention mechanism fashioned in accordance with the present principles. The spinal interbody implant 110 comprises an implant 112 and a bone screw retention mechanism defined by a bone screw retention plate assembly 114 and a configured retention plate reception area 130 formed in a posterior face 125 of the implant 112.

The implant 112 is defined a body 120 that is fabricated from a bio-compatible material such as stainless steel, titanium, a titanium alloy, composite, polymer or the like. The implant body 120 is sized to be received between adjacent vertebrae but to not extend beyond the periphery of the vertebra. As such, the implant body 120 may be fabricated in various sizes to accommodate various sizes of vertebrae.

The implant body 120 has an essentially D-shaped wall 122 with a serrated upper surface 123 and a like serrated lower surface (not seen in the figures). The D-shaped wall 122 defines an essentially D-shaped void 124 within its interior. The implant body 120 has several bone screw pockets or bores 126, 127, 128 each of one which is configured to receive a bone screw 60 therein. Particularly, the implant body 120 has a middle bone screw pocket or bore 126 that extends from the posterior face 125 and angles downwardly (in the inferior direction when implanted) into the void 124, a first lateral bone screw pocket or bore 127 that extends from the posterior face 125 and angles upwardly (in the superior direction when implanted) into the void 124, and a second lateral bone screw pocket or bore 128 that extends from the posterior face and angles upwardly (in the superior direction when implanted) into the void 124. It should be appreciated that the nomenclature first and second is arbitrary. The bone screw pockets 126, 127, 128 allow the shank of a bone screw to extend through and out of the respective bore but not allow the heads thereof to ingress into the void 124.

A bone screw 60a is shown extending through and captured by the middle bone screw bore 126. Particularly, the threaded shank 61a of the bone screw 60a extends at a downward angle from the implant body 120 due to the angle of the bone screw bore 126 while the head 62a is captured in the bone screw pocket 126. The head 62a has a hexagonal bore 63a for receipt of a hexagonal tool (not shown) in order to install the bone screw 60a. In like manner, a bone screw 60b is shown extending through and captured by the first lateral bone screw bore 127. Particularly, the threaded shank 61b of the bone screw 60b extends at an upward angle from the implant body 120 due to the angle of the bone screw bore 127 while the head 62b is captured in the bone screw pocket 127. The head 62b also has a hexagonal bore 63a for receipt of a hexagonal tool (not shown) in order to install the bone screw 60a. Again in like manner, a bone screw 60c is shown extending through and captured by the second lateral bone screw bore 128. Particularly, the threaded shank 61c of the bone screw 60c extends at an upward angle from the implant body 120 due to the angle of the bone screw bore 128 while the head 62c is captured in the bone screw pocket 128. The head 62c also has a hexagonal bore 63c for receipt of a hexagonal tool (not shown) in order to install the bone screw 60c.

The implant body 120 further includes a first configured notch 136 formed in a first front lateral corner thereof and a second configured notch 137 formed in a second front lateral corner thereof. Again, it should be appreciated that the nomenclature first and second is arbitrary. The first and second configured notches 136, 137 are situated on and shaped so as to allow the implant body 120 to be implanted between adjacent vertebrae (not shown) via an implant tool (not shown).

Figure 9:
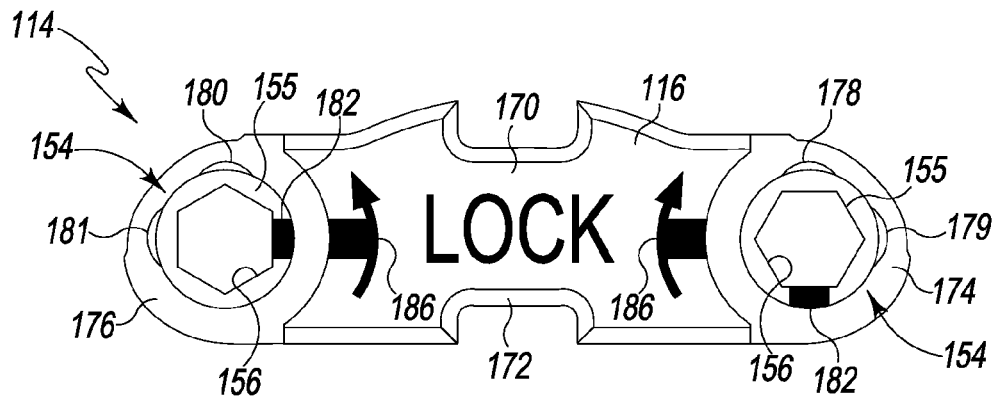
FIG. 9 is a front plan view of the bone screw retention plate and installed retention fasteners, the view additionally illustrating how the indicia of both provides a visual indication of the locked and unlocked positions of the retention plate.
Figure 10:
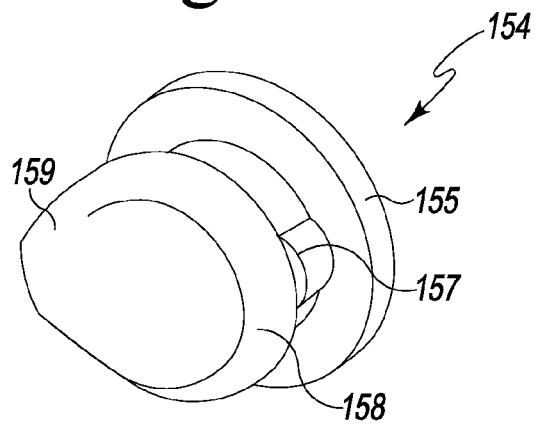
FIG. 10 is an isometric view of a retention fastener of the bone screw retention mechanism.
Figure 11:
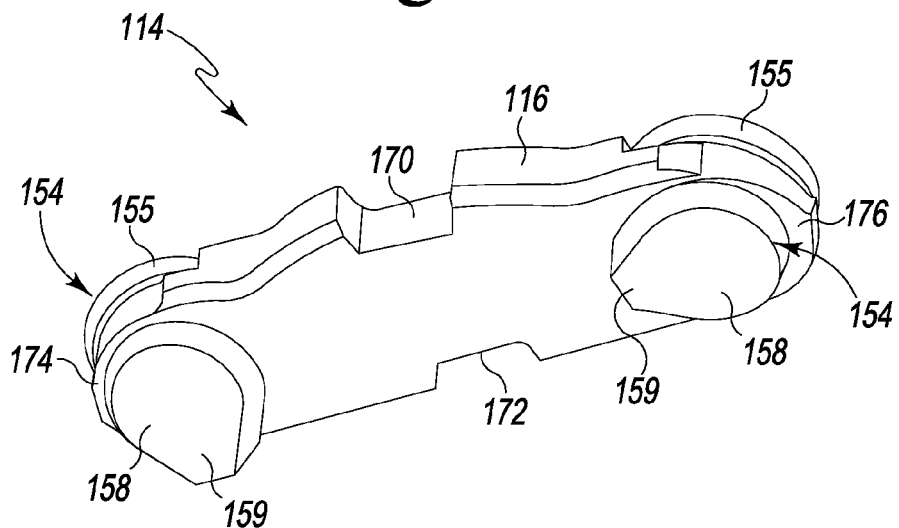
FIG. 11 is a top isometric view of the retention plate and retention plate fasteners of the present bone screw retention mechanism.
Figure 12:
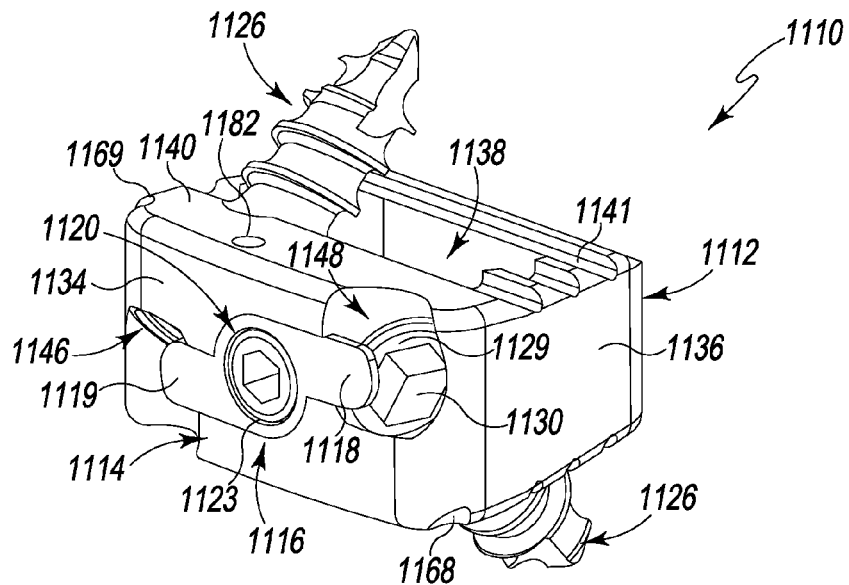
FIG. 12 is a perspective view of another spinal interbody implant with having another embodiment of a bone screw retention mechanism fashioned in accordance with the present principles, the spinal interbody implant shown as it would look like if implanted in a spine with bone screws therein and a lock plate assembly of the bone screw retention mechanism installed thereon.
Figure 13:
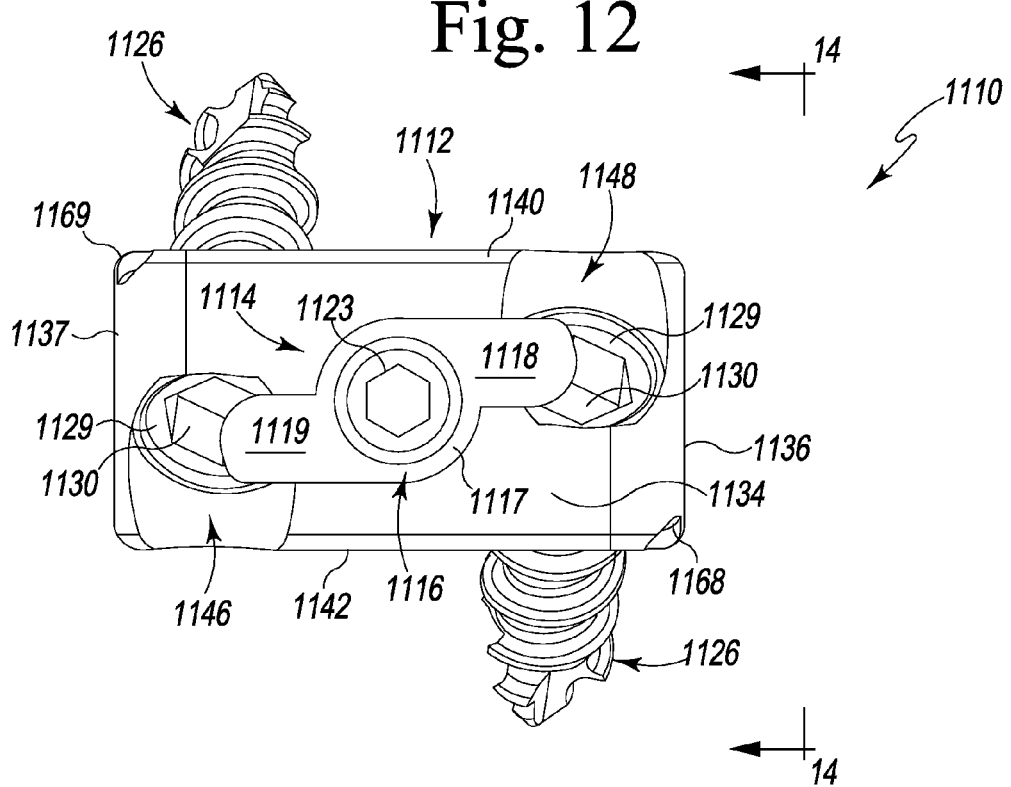
FIG. 13 is a front view of the spinal interbody implant of FIG. 12 as taken along line 13-13 of FIG. 14.
Figure 14:
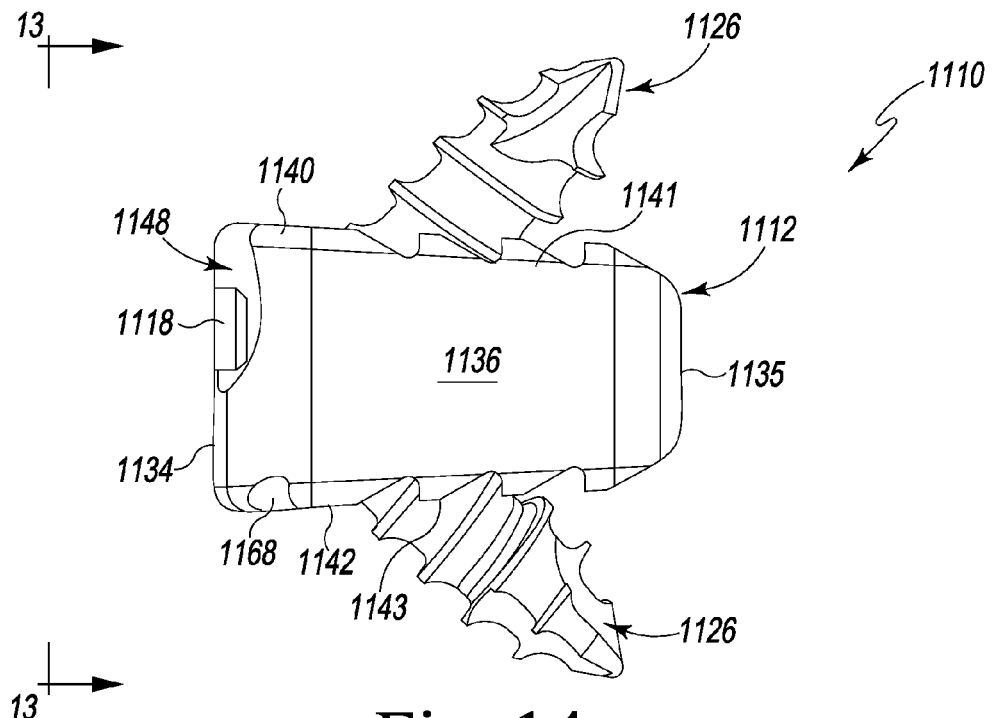
FIG. 14 is a side view of the spinal interbody implant of FIG. 12 as taken along line 14-14 of FIG. 13.
Figure 15:
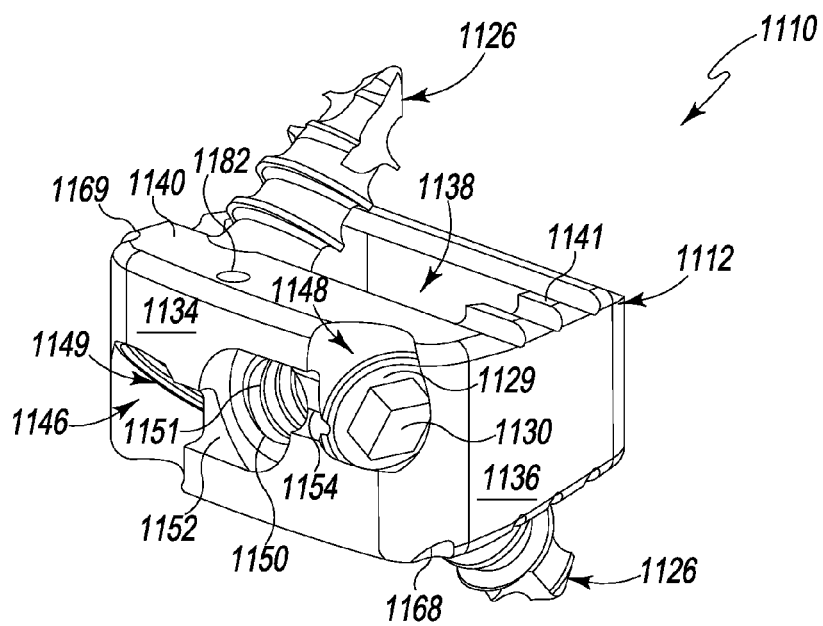
FIG. 15 is a perspective view of the spinal interbody implant of FIG. 12 with the bone screw retention plate removed.
Figure 16:
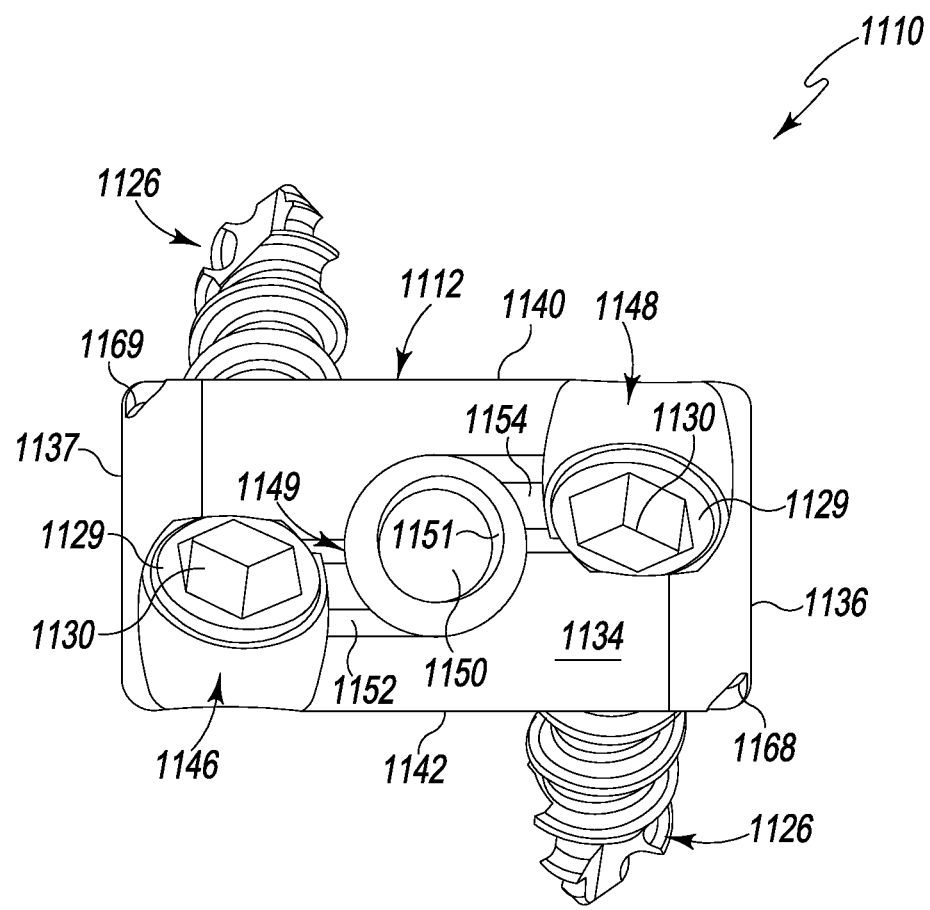
FIG. 16 is a front view of the spinal interbody implant of FIG. 15.

With particular reference to FIGS. 9-11, the retention plate mechanism 114 includes a generally elongated oval retention plate 116 and two retention plate fasteners 154 all of which are fabricated from a bio-compatible material such as stainless steel, titanium, a titanium alloy, composite, polymer or the like. The retention plate 116 has a first end boss 174 having a bore in which is situated a first retention plate fastener 154 and a second end boss 176 having a bore in which is situated a second retention plate fastener 154. The first and second retention plate fasteners 154 are the same and are each able to rotate within its end boss bore—as described more fully below.

Additionally, the plate 116 has an upper notch 170 and a lower notch 172 each disposed essentially midway between the first and second end bosses 174, 176. The upper and lower notches 170, 172 allow the retention plate 116 to be installed and/or uninstalled using an installation tool (not shown).

As best seen in FIGS. 9-11, the retention plate fastener or cam 154 has a circular first end 155 with a hexagonal bore 156 for receipt of a hexagonal tool (not shown) in order to rotate the fastener 154 while the retention plate fastener 154 is situated in the end boss bores of the retention plate 116. A nose 159 is provided at the second end of the cam 154 while a nub 157 is situated between the first and second ends. As seen in FIG. 9, the bore of the first end boss 174 has first and second indents 178, 179 that are situated 90° relative to one another about the first end boss bore. The bore of the second end boss 176 likewise has first and second indents 180, 181 that are situated 90° relative to one another about the second end boss bore. The nub 157 of the fastener provides two secure rotational positions of the cam 154 within the boss bore and thus relative to the retention plate 116 by thy nub 157 resting in one of the two indents of the boss bore. One indent/position provides an unlocked position or state of the cam 154 while the other indent/position provides a locked position or state of the cam 154. Additionally, when the cam 154 is turned or rotated, the nub 157 applies pressure to the boss bore wall thus causing it to deflect. This provides a resistance to spontaneous and/or induced rotation of the cam 154.

The locked and unlocked positions of the cam 154 are relative to the nose 159 of the cam in relationship to the retention plate reception area 130 and particularly with respect to undercuts 188 and 190 of the retention plate reception area 130. As indicated above, the retention area 130 of the implant body 120 is configured to receive the retention plate assembly 114 after the bone screws 60a, 60b and 60c have secured the implant body 120 to adjacent upper and lower vertebrae of the spine (not shown). In FIG. 11, the nose 159 of the cam 154 of the first end boss 174 points downwardly indicating that the cam 154 is in the unlocked position, while the nose 159 of the cam 154 of the second end boss 176 points laterally inward indicating that the cam is in the locked position. As described more fully below, the cam 154 includes indicia on the end 155 for a visual indication of the locked and unlocked positions.

Figure 6:
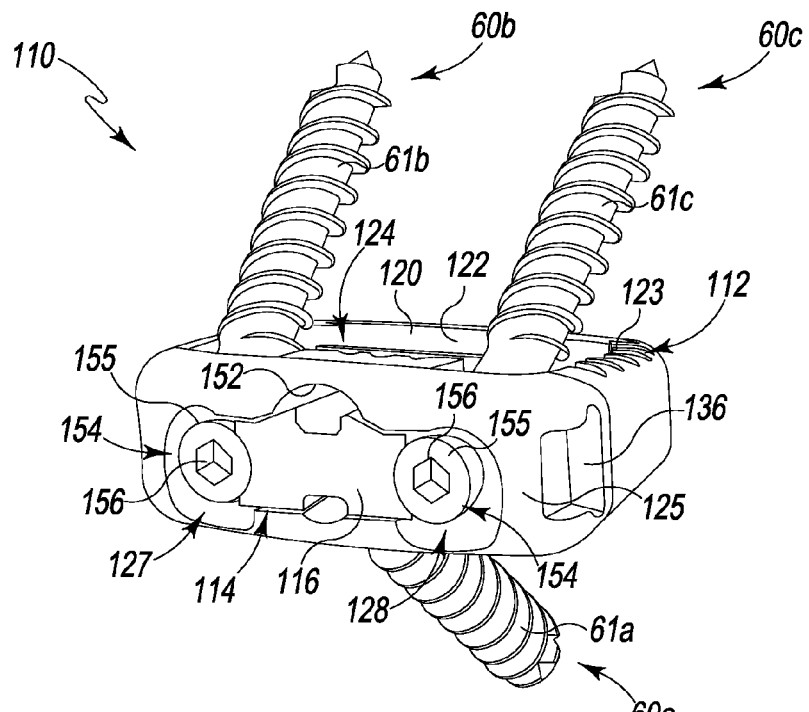
FIG. 6 is an isometric view of another spinal interbody implant incorporating a bone screw retention mechanism with the bone screw retention plate and retention fasteners thereof installed and in the locked position, with bone screws for installing the spinal interbody implant shown installed in the implant.
Figure 7:
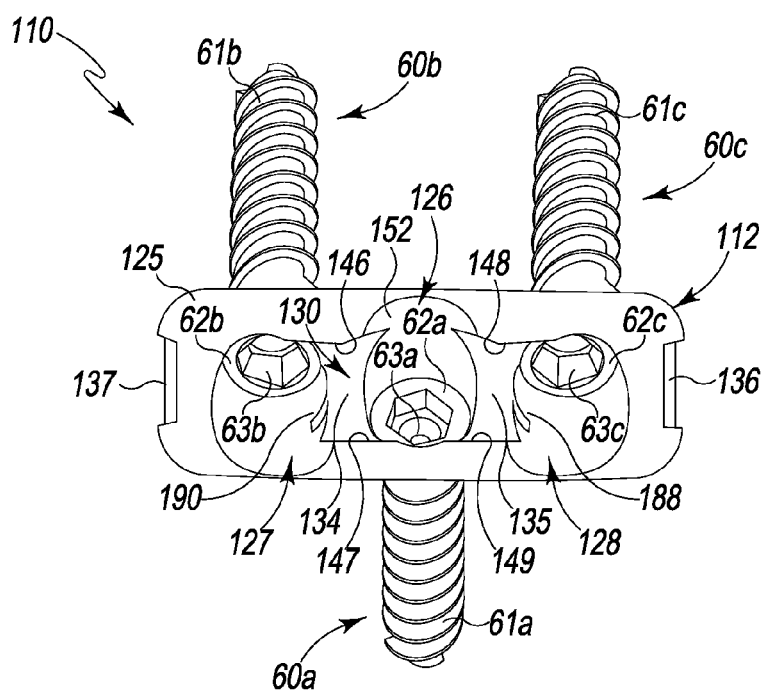
FIG. 7 is a front plan view of the spinal interbody implant of FIG. 6 with the bone screw retention plate and retention fasteners removed.
Figure 8:
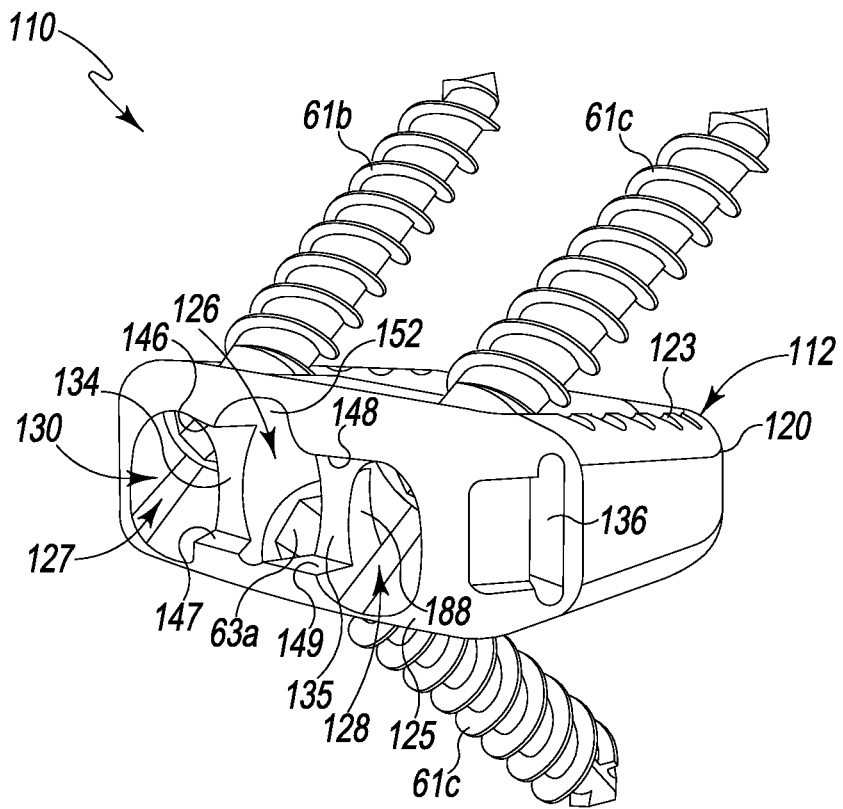
FIG. 8 is a side isometric view of the spinal interbody implant as shown in FIG. 7.

As best seen in FIG. 7, the retention area 130 is defined in the front face 125 of the implant body 120. The front face 125 has a slight curvature which is likewise provided by the retention area 130. The retention area 130 consists of a first undercut area 188 in a lateral side of the second lateral bone screw bore 128, a second undercut area 190 in a lateral side of the first lateral bone screw bore 127, a first intermediate channel 135 defined between upper and lower ledges 148, 149, and a second intermediate channel 134 defined between upper and lower ledges 146, 147. Again, the nomenclature first and second is arbitrary. The retention plate 16 thus has a height that is received in the first and second intermediate channels 135, 134 between the respective ledges 148, 149 and 146, 147. FIG. 6 shows the retention plate assembly 114 installed into the implant body 112 with the cams 154 in the locked position.

The retention plate assembly 114 is installed after the bone screws 60 have properly secured the implant 110. Initially, the cams 154 of the retention plate assembly 114 are in the unlocked position. Once the retention plate assembly 114 has been properly installed into the retention plate area 130 the cams 154 are rotated or turned from the unlocked position to the locked position. This rotates the nub 157 from one indent to another to provide a positive retention of the cam 154 in the unlocked and locked positions, and also rotates the nose 159 into the respective undercut 188 or 190. The back side/surface of the retention plate 116 is adjacent to and/or abuts at least a portion of the heads of the installed bone screws 60 such that back out of an installed bone screw is not possible. The retention plate thus provides a barrier against the backing out of the installed bone screws.

The retention plate assembly 114 also provides a visual indication of its locked and unlocked positions, states or modes. As best seen in FIG. 9, the cams 154 have a mark or indicia 182 (e.g. line) that corresponds to whether the nose 157 of the cam 154 is pointing downward (as is the case of the cam 154 of the end boss 174) and thus is in an unlocked position or whether the nose 157 of the cam 154 is pointing sideways (as is the case of the cam 154 of the end boss 176 and thus is in a locked position. The retention plate 116 may moreover include separate indicia 184, 186 that shows the rotational direction for locking the cams (via a curved arrow) and provides a confirmation of the locked position for the cam by a line that will align with the indicia 182 of the cam.

Referring to the FIGS. 12-22 there is depicted another exemplary spinal interbody implant, generally designated 1110, that incorporates a bone screw retention mechanism fashioned in accordance with the present principles. The spinal interbody implant 1110 comprises an implant or implant body 1112 and a bone screw retention mechanism/assembly 1114.

The implant body 1112 is made from a bio-compatible material such as stainless steel, titanium, a titanium alloy, composite, polymer or the like. The implant body 1112 is sized to be received between adjacent vertebrae of the spine but to not extend beyond the periphery of the vertebra. As such, the implant body 1112 may be fabricated in various sizes to accommodate various sizes of vertebrae.

The implant body 1112 is essentially D-shaped and defining an essentially D-shaped void or cavity 1138 within its interior. As such, the implant body 1112 has a posterior (front) side or face 1134, an anterior (rear) side or face 1135, a medial (side) side or face 1137, and a lateral (side) side or face 1136. An upper, top or superior surface 1140 of the implant body 1112 includes a plurality of serrations or teeth 1141 that extend laterally across the superior surface 1140. In like manner, a lower, bottom or inferior surface 1142 of the implant body 1112 includes a plurality of serrations or teeth 1143 that extend laterally across the inferior surface 1143.

The implant body 1112 has two bone screw bores 1146, 1148 both of which are configured to receive a bone screw 1126 in order to retain the implant body 1112 in a desired orientation and/or position when implanted in the spine. The bone screw 1126 has a shank 1127 with a tip 1131, a generally ovate head 1129, and external threads/threading 1128. The head 1129 has a configured socket 1130 that is shown having a hexagonal shape. The implant body 1112 has a lateral bone screw bore 1146 that extends from the posterior face 1134 thereof and angles upwardly (in the superior direction when implanted) into the void 1138, and a medial bone screw bore 1148 that extends from the posterior face 1134 and angles downwardly (in the inferior direction when implanted) into the void 1138. The bone screw bores 1146, 1148 allow the shank 1127 to pass and extend therethrough but does not allow the head 1129 to pass therethrough. Rather, the head 1129 engages the bore to attach the implant body to the appropriate vertebrae (i.e. a superior vertebra for the bone screw in the lateral bone screw bore 1146, and an inferior vertebra for the bone screw in the medial bone screw bore 1148.

Figure 17:
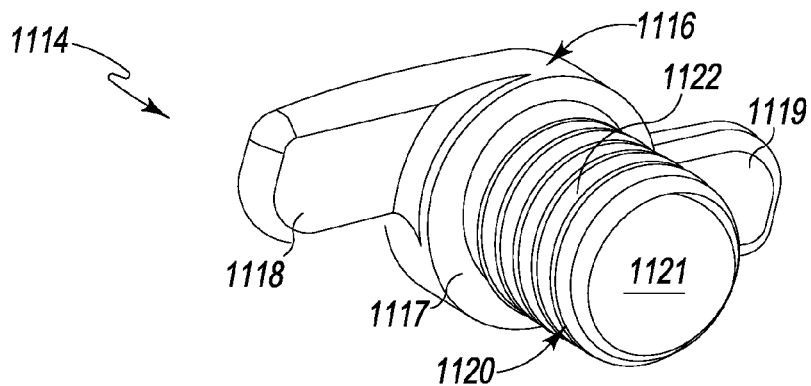
FIG. 17 rear perspective view of the lock plate assembly of the bone screw retention mechanism.
Figure 18:
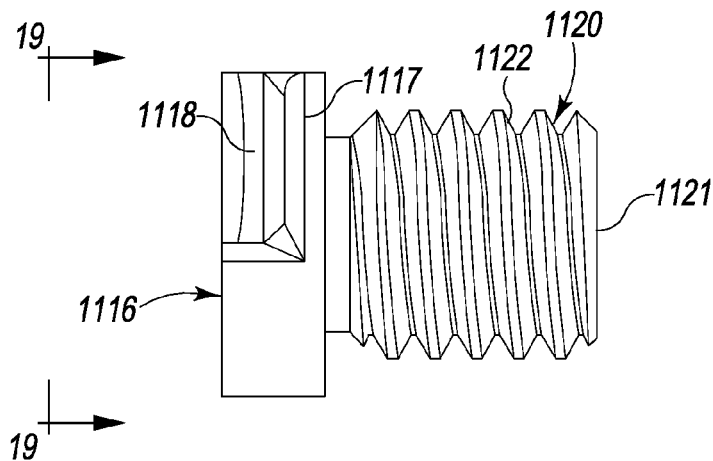
FIG. 18 is a side view of the lock plate assembly of FIG. 17.
Figure 19:
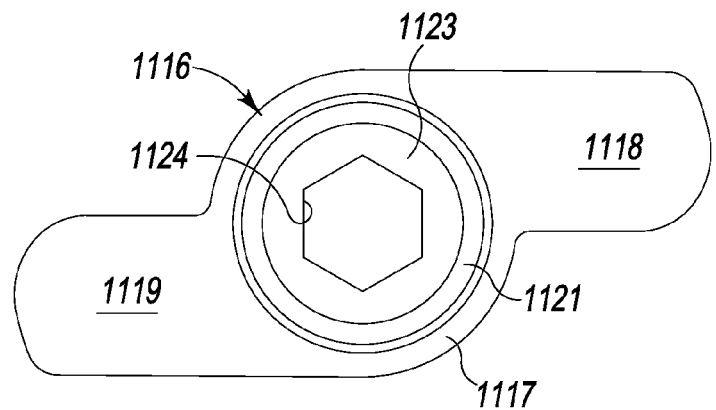
FIG. 19 is a front view of the lock plate assembly of FIG. 17 as taken along line 19-19 of FIG. 18.

The bone screw retention mechanism 1114 is characterized by a bone screw retention plate 1116, a bolt (or other appropriate fastener) 1120, and a configured retention plate reception area 1149 formed in the posterior face 1134 of the implant body 1112. The bone screw retention plate 1116 and bolt 1120 are best seen in FIGS. 17-19. The retention plate 1116 has a thickness that either allows the retention plate to be flexible but resilient or be rigid and is made from a bio-compatible material such as stainless steel, titanium, a titanium alloy, composite, polymer or the like in a manner that allows such flexibility/resiliency.

The retention plate 1116 is characterized by a generally round hub 1117 having a first or medial arm 1118 extending from one side of the hub 1117, and a second or lateral arm 1119 extending from another side of the hub 1117 diametrically opposite the first arm 1118, the arms 1118, 1119 having rounded ends. The arms 1118, 1119 are of a length sufficient to extend over at least a portion of the head of an installed bone screw (see e.g. FIGS. 12 and 13). The hub 1117 has a bore that is sized to receive the fastener/bolt 1120. The bolt 1120 has a shank 1121 with external threading 1122. While the shank 1121 of the bolt 1120 extends through the hub bore, the head 1123 of the bolt is retained by the bore.

The configured retention plate reception area 1149 of the implant body 1112 is configured to receive the retention plate 1116 particularly after bone screws 1126 have secured the implant body 1112 to the adjacent upper (superior) and lower (inferior) vertebrae (not shown). The retention area 1149 is defined in the front face 1134 of the implant body 1112. The front face 1134 is generally planar with a slight curvature. The retention area 1149 consists of a central inset/bore 1150 having internal threading 1151, a lateral channel or slot 1152 in communication with and extending from a side of the central inset/bore 1150, and a medial channel or slot 1154 in communication with and extending from another side of the central inset/bore diametrically opposite the slot 1152. The hub 1117 of the retention plate 1116 is sized to be received in the inset and about the bore 1150, while the threaded shank 1122 is threadedly received in the bore to hold the retention plate 1116 to the implant body 1112. The lateral slot 1152 is sized to receive the arm 1119 of the retention plate 1116, while the slot 1154 is sized to receive the arm 1118 of the retention plate 1116.

Once the implant body 1112 has been implanted and secured with bone screws 1126, the retention plate 1116 is situated into the retention area 1149 and the bolt 1120 threaded into the bore 1150 though use of a tool in the bolt head socket 1124. The arms 1118, 1119 extend over the heads of the bone screws to prevent the screws from backing out. Particularly, the back side/surface of the arms 1118, 1119 is adjacent to and/or abuts at least a portion of the heads of the installed bone screws such that back out of an installed bone screw is not possible. The retention plate 1116 thus provides a barrier against the backing out of the installed bone screws.

Figure 20:
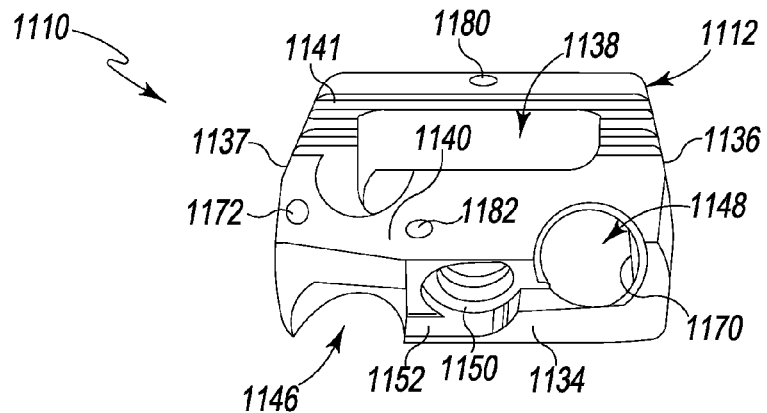
FIG. 20 is an upper perspective view of the spinal interbody implant of FIG. 12 sans bone screws particularly illustrating stop pins for preventing over advancement of the bone screw during bone screw insertion.
Figure 21:
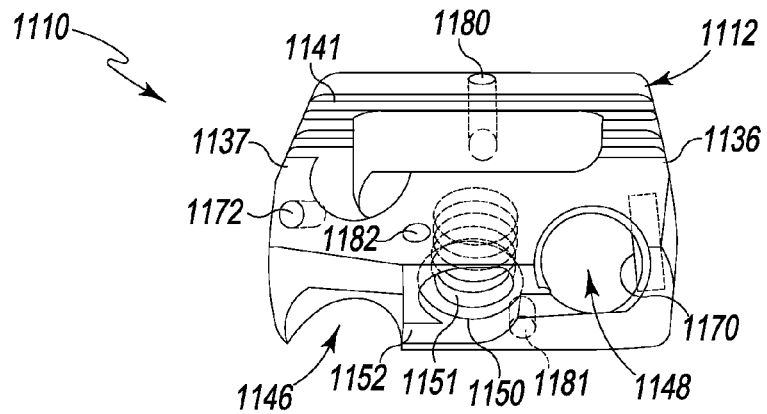
FIG. 21 is the upper perspective view of the spinal interbody implant of FIG. 12 with the body thereof in "ghost" in order to particularly show placement of the stop pins relative to the bone screw bores of the interbody implant.
Figure 22:
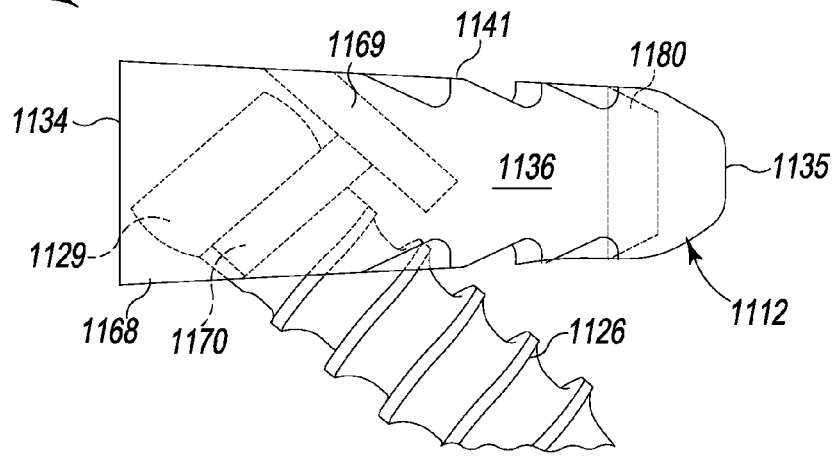
FIG. 22 is an enlarged side view of the spinal interbody implant of FIG. 21 with a bone screw inserted therein particularly showing position of the stop pin relative to the inserted bone screw.

As seen in FIGS. 20-22, the present implant 1110 has a feature to prevent over advancement of the bone screws 1126 through the bone screw bores 1146, 1148. Particularly, stop pin 1170, positioned in bore 1168, prevents a bone screw 1126 from over advancement within the bone screw bore 1148. Stop pin 1172, positioned in bore 1169, prevents a bone screw 1126 from over advancement within the bore 1146. The stops pins 1170, 1172 are positioned within the (PEEK) interbody implant 1110 such that they seat slightly below the spherical diameter of the screw pocket (where the head of the bone screw sits) and partially protrudes out into the bone screw's trajectory to create a barrier that comes into contact only with the spherical head of the screw to prevent over advancement and ensure seating of the bone screw within the screw pocket.

Moreover, the spinal interbody implant 1110 includes various bores for receiving and accommodating radiographic tantalum markers. Particularly, the body 1112 has three such bores, bores 1180, 1181 and 1182. Bore 1180 is in the anterior end of the implant. Particularly, bore 1180 extends through the anterior end 1135 of the implant from the superior side to the inferior side thereof. Bores 1181 and 1182 are in the posterior end 1134 of the implant. Bore 1181 extends from the inferior surface of the implant into the body 1112. Bore 1181 extends from the superior surface of the implant into the body 1112. While not shown, radiographic tantalum markers may be implanted into the bores.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal interbody implant comprising:
    a body having a top surface, a bottom surface, a front face, a rear face, and first and second sides, wherein the top surface and the bottom surface are configured to engage vertebral bone material of adjacent vertebrae;
    first and second bone screw bores extending through the body and configured to enable threading rotation of a first bone screw within the first bone screw bore and a second bone screw within the second bone screw bore such that the first and second bone screws engage the vertebral bone material;
    a cutout formed in the front face and extending between the first and second bone screw bores;
    a plate configured for reception in the cutout after the first and second bone screws are received in the first and second bone screw bores, the plate extending over the first and second bone screw bores to prevent the first and second bone screws from backing out of the first and second bone screw bores;
    a first stop pin disposed within the body and configured to engage only a head of the first bone screw during rotation of the first bone screw within the first bone screw bore to limit advancement of the first bone screw through the body, wherein the first stop pin is received within a first stop pin bore extending from the top surface;
a second stop pin disposed within the body and configured to engage only a head of the second bone screw during rotation of the second bone screw within the second bone screw bore to limit advancement of the second bone screw through the body, wherein the second stop pin is received within a second stop pin bore extending from the bottom surface; and
a threaded fastener extending through the plate and configured to secure the plate in position within the cutout.

2. The spinal interbody implant of claim 1, wherein an outer surface of the plate is flush with the front face of the body when the plate is received within the cutout.

3. The spinal interbody implant of claim 1, wherein the top surface of the body includes serrated portions extending adjacent the rear face and the first and second sides.

4. The spinal interbody implant of claim 3, wherein the serrated portions at least partially define a void in the top surface.

5. The spinal interbody implant of claim 4, wherein the void extends from the top surface to the bottom surface.

6. The spinal interbody implant of claim 1, wherein at least one of the first and second bone screw bores extends through both the front face and the top surface.

7. A spinal interbody implant comprising:
a body having a top surface, a bottom surface, a front face, a rear face, and first and second sides, wherein the top surface and the bottom surface are configured to engage vertebral bone material of adjacent vertebral bodies;
a bone screw bore extending through the body and configured to receive a bone screw and enable rotation of the bone screw within the bone screw bore such that the bone screw engages the vertebral bone material of at least one of the adjacent vertebral bodies;
a cutout formed in the front face and extending from the bone screw bore;
a stop pin disposed within the body and configured to engage only a head of the bone screw during rotation of the bone screw within the bone screw bore to limit advancement of the bone screw through the body, wherein the stop pin is received within a stop pin bore extending from at least one of the top surface and the bottom surface; and
a plate configured for reception in the cutout after a bone screw has been received in the bone screw bore;
a fastener extending through the plate to secure the plate to the body.

8. The spinal interbody implant of claim 7, wherein the top surface of the body includes serrated portions extending adjacent the rear face and the first and second sides.

9. The spinal interbody implant of claim 8, wherein the serrated portions at least partially define a void in the top surface.

10. The spinal interbody implant of claim 9, wherein the void extends from the top surface to the bottom surface.

11. The spinal interbody implant of claim 7, wherein the bone screw bore extends through both the front face and the top surface.

12. A spinal interbody implant comprising:
a body having a top surface, a bottom surface, a front face, a rear face, and first and second sides;
first and second bone screw bores extending through the body; and
a cutout formed in the front face and extending between the first and second bone screw bores;
a first stop pin disposed within the body and configured to engage only a head of a first bone screw during rotation of the first bone screw within the first bone screw bore to limit advancement of the first bone screw through the body;
a second stop pin disposed within the body and configured to engage only a head of a second bone screw during rotation of the second bone screw within the second bone screw bore to limit advancement of the second bone screw through the body;
a plate received configured to be received within the cutout and be secured to the body with a fastener extending through the plate;
wherein the first stop in extends in a non-parallel fashion relative to the second stop pin.

13. The spinal interbody implant of claim 12, wherein the first and second bone screw bores are at least partially circular.

14. The spinal interbody implant of claim 12, wherein the plate is configured to retain first and second bone screws with the first and second bone screw bores, respectively.

15. The spinal interbody implant of claim 14, wherein the body is a unitary structure.

16. The spinal interbody implant of claim 15, wherein the top surface of the body includes serrated portions extending adjacent the rear face and the first and second sides.

17. The spinal interbody implant of claim 16, wherein the serrated portions at least partially define a void in the top surface.

* * * * *